(12) United States Patent
Hungr et al.

(10) Patent No.: US 12,350,425 B2
(45) Date of Patent: Jul. 8, 2025

(54) LUMINOUS RESPIRATORY VENTILATION DEVICE

(71) Applicant: SLEEPINNOV TECHNOLOGY, Moirans (FR)

(72) Inventors: Nikolaï Hungr, Moirans (FR); Jérôme Argod, Moirans (FR); Marc Lantelme, Moirans (FR); Nicolas Gaiffe, Moirans (FR)

(73) Assignee: SLEEPINNOV TECHNOLOGY, Moirans (FR)

( * ) Notice: Subject to any disclaimer, the term of this patent is extended or adjusted under 35 U.S.C. 154(b) by 940 days.

(21) Appl. No.: 17/437,197

(22) PCT Filed: Mar. 6, 2020

(86) PCT No.: PCT/FR2020/050465
§ 371 (c)(1),
(2) Date: Sep. 8, 2021

(87) PCT Pub. No.: WO2020/183097
PCT Pub. Date: Sep. 17, 2020

(65) Prior Publication Data
US 2022/0168525 A1    Jun. 2, 2022

(30) Foreign Application Priority Data

Mar. 8, 2019 (FR) ...................................... 1902418

(51) Int. Cl.
*A61M 16/00* (2006.01)
*F21S 10/02* (2006.01)
(Continued)

(52) U.S. Cl.
CPC ...... *A61M 16/024* (2017.08); *A61M 16/0003* (2014.02); *A61M 16/0051* (2013.01);
(Continued)

(58) Field of Classification Search
CPC ...... A61M 16/0057–0075; A61M 16/06–0655
See application file for complete search history.

(56) References Cited

U.S. PATENT DOCUMENTS 8,453,640 B2   6/2013  Martin et al.
2005/0235993 A1  10/2005  Baecke et al.
(Continued)

FOREIGN PATENT DOCUMENTS

CN    107929895 A       4/2018
EP    2371411 A1 * 10/2011 ........ A61M 16/0051
(Continued)

OTHER PUBLICATIONS

International Search Report for International Application No. PCT/FR2020/050465, mailed Aug. 5, 2020, 7 pages (With English Translation).
(Continued)

*Primary Examiner* — Joseph D. Boecker
*Assistant Examiner* — Thomas W Greig
(74) *Attorney, Agent, or Firm* — TraskBritt (57) ABSTRACT

A respiratory ventilation device—configured to send an airflow, generated by a fan, into a duct that extends between the device and a breathing mask configured to be worn by a user—comprises an air inlet intended to admit air into the device; a fan; and an air outlet configured to be connected to the duct, such that, when the fan is in operation, the air flows from the air inlet successively toward the fan and then toward the air outlet. The device also comprises a flow rate sensor configured to measure a flow rate of air circulating through the device, and/or a pressure sensor configured to measure a pressure between the fan and the air outlet. A control unit is connected to the flow rate sensor and/or to the pressure sensor. The device also includes at least one source of light.

19 Claims, 7 Drawing Sheets

(51) Int. Cl.
 *F21V 5/00* (2018.01)
 *F21V 7/04* (2006.01)
 *F21V 33/00* (2006.01)
(52) U.S. Cl.
 CPC ...... *A61M 16/0057* (2013.01); *A61M 16/026* (2017.08); *F21S 10/02* (2013.01); *F21V 5/00* (2013.01); *F21V 7/04* (2013.01); *F21V 33/0068* (2013.01); *A61M 2016/0027* (2013.01); *A61M 2016/0033* (2013.01); *A61M 2205/584* (2013.01); *A61M 2205/587* (2013.01); *A61M 2230/06* (2013.01); *A61M 2230/42* (2013.01)

(56) References Cited

U.S. PATENT DOCUMENTS

| | | |
|---|---|---|
| 2007/0023044 A1 | 2/2007 | Kwok et al. |
| 2007/0193582 A1 | 8/2007 | Kwok et al. |
| 2011/0308518 A1 | 12/2011 | McGroary et al. |
| 2015/0190605 A1* | 7/2015 | Martin ............ A61M 16/1075 128/203.27 |
| 2017/0119919 A1 | 5/2017 | Hsiao |
| 2018/0126104 A1 | 5/2018 | Krüger et al. |

FOREIGN PATENT DOCUMENTS

| | | |
|---|---|---|
| WO | 2011/006199 A1 | 1/2011 |
| WO | 2012/106775 A1 | 8/2012 |
| WO | WO-2019075513 A1 * | 4/2019 |

OTHER PUBLICATIONS

International Written Opinion for International Application No. PCT/FR2020/050465, mailed Aug. 5, 2020, 11 pages (With English Machine Translation).

* cited by examiner

LUMINOUS RESPIRATORY VENTILATION DEVICE

CROSS-REFERENCE TO RELATED APPLICATIONS

This application is a national phase entry under 35 U.S.C. § 371 of International Patent Application PCT/FR2020/050465, filed Mar. 6, 2020, designating the United States of America and published as International Patent Publication WO 2020/183097 A1 on Sep. 17, 2020, which claims the benefit under Article 8 of the Patent Cooperation Treaty to French Patent Application Serial No. 1902418, filed Mar. 8, 2019.

TECHNICAL FIELD

The technical field of the disclosure is a ventilation device employing continuous positive airway pressure (CPAP). This type of device is commonly used in the treatment of sleep apnea.

BACKGROUND

The use of CPAP ventilation is a standard treatment in the field of sleep apnea. This treatment consists in continuously blowing air into a mask applied to the face of a user. It may be a nose, nasal or face mask. The flow of air reaches the user's respiratory tract, exerting sufficient pressure thereon to prevent the formation of a collapse.

These CPAP ventilation devices are used at night. Therefore, they must be as quiet as possible. Among the prior-art devices mention may, for example, be made of the device described in U.S. Pat. No. 8,453,640. Such a device is portable and has a substantially cylindrical shape, extending from a planar base.

Document EP2371411 describes a CPAP device comprising one or more light sources, arranged on a tube that opens onto a mask or onto the casing of the device. Document WO2012106775 describes a CPAP device comprising light sources that may be modulated depending on an air flow rate. The light sources are placed either on the mask or on a casing. Document US2018126104 describes a ventilation device that allows a cough attack to be detected, and then triggers an alarm. This device comprises a light source placed on a casing.

Other types of ventilation devices are described in WO2011006199, US20050235993, US20070023044, US20070193582 or US20110308518.

A ventilatory breathing device has been designed that has additional functionalities compared to the devices currently available.

BRIEF SUMMARY

A first subject of the disclosure is a respiratory ventilation device, intended to send an airflow, generated by a fan, into a duct, the duct extending between the device and a respiratory mask intended to be worn by a user, the device comprising:
  an air inlet, intended to admit air into the device;
  a fan;
  an air outlet, the air outlet being configured to be connected to the duct;
  such that when the fan is operating, air flows, through the device, from the air inlet successively to the fan then to the air outlet;

the device also comprising:
  a flow sensor, measuring a flow rate of air flowing through the device, and/or a pressure sensor measuring a pressure between the fan and the air outlet,
  a control unit, connected to the flow sensor and/or to the pressure sensor;
the device being characterized in that it comprises one of the following features, alone or in technically feasible combinations:
  The device comprises at least one light source, able to emit a light that propagates outside of the device, the light source being driven by the control unit, such that the control unit is configured to activate the light source depending on the flow rate of air measured by the flow sensor and/or on the pressure measured by the pressure sensor. By driven, what is meant is control of the intensity of the light source and/or control of the color of the emitted light.
  The control unit is configured to modulate a color of the light emitted by the light source, or by each light source.
  The control unit is configured to modulate a light intensity and/or a color of the light source, or of each light source, with a modulation period, the modulation period comprising:
    a gradual increase in light intensity followed by a gradual decrease in light intensity;
    and/or a gradual variation in color between a start color and an end color, followed by a gradual variation in the color of the emitted light between the end color and the start color.
  The modulation period may be adjustable.
  The control unit is configured to:
    estimate a respiratory rate depending on the flow rates measured by the flow sensor;
    define the modulation period depending on the estimated respiratory rate.
  The control unit is configured to:
    estimate a heart rate depending on the flow rates measured by the flow sensor;
    define the modulation period depending on the estimated heart rate.
  The control unit is configured to activate the light source, or each light source, in an alarm sequence, when the air flow rate is outside of a predetermined flow-rate range, or when the air flow rate is greater or less than a predefined flow-rate threshold value.
  The control unit is configured to determine a variation as a function of time in the flow rates measured by the flow sensor, at various successive times, and to activate the light source, or each light source, in an alarm sequence, when the variation as a function of time is less than a variation threshold, the latter preferably being predefined.
  The control unit is configured to activate the light source, in an alarm sequence, when the air pressure is outside of a predetermined pressure range, or is less or less than a predefined pressure threshold value.
  The device comprises an enclosure, defining the air inlet and the air outlet, the enclosure containing the fan,
    the enclosure extending, around a longitudinal axis, between a base and a top;
    the enclosure comprising a side wall connecting the base and the top, the side face extending around the longitudinal axis;
    the enclosure comprising at least one holder, forming a curve, and extending inside the enclosure, around the longitudinal axis, the holder being placed facing the side wall, the holder bearing a plurality of light sources, each light source being configured to emit a light;

the enclosure being formed from a translucent and/or scattering material;

such that under the effect of an activation of the light sources fastened to the holder, the light, produced by the light sources, diffuses through the side wall of the enclosure.

The side wall extends around the longitudinal axis at a first radius.

The enclosure contains a reflector of light, the reflector extending around the longitudinal axis, at a second radius less than the first radius, such that the reflector is able to reflect a light produced by the light sources toward the enclosure.

The light sources are configured to emit a light in the direction of the top of the enclosure.

At least one light source, or even each light source, emits a light in an emission cone extending around an emission axis, the emission axis of the light source, or of each light source, being oriented in the direction of the top of the enclosure.

The light sources are spaced apart around the longitudinal axis.

At least one light source, or even each light source, lies between the holder and the longitudinal axis, such that the holder is interposed between at least one light source, or even each light source, and the enclosure.

The enclosure comprises a clock, connected to the control unit, such that the control unit is configured to modulate a light intensity and/or the color of the light of the light sources depending on the clock.

A second subject of the disclosure is a method for controlling a light source of a device according to the first subject of the disclosure, comprising the following steps:

a) measurement of flow rates using the flow sensor and/or of pressures using the pressure sensor at various measurement times, respectively;

b) depending on the measured flow-rate and/or pressure values, activation of the light source with the control unit.

According to one embodiment, in step b), the activation of the light source is configured to modulate a light intensity and/or a color of the light source with a modulation period, the modulation period comprising a gradual increase in light intensity followed by a gradual decrease in light intensity and/or a gradual variation in color between a start color and an end color, followed by a gradual variation in the color of the emitted light between the end color and the start color.

According to one embodiment, step a) comprises a measurement of flow rates at various measurement times, and an estimation of a respiratory rate depending on the measured flow rates, such that, in step b), the modulation period is defined depending on the estimated respiratory rate.

According to one embodiment, step a) comprises a measurement of flow rates at various measurement times, and an estimation of a heart rate depending on the measured flow rates, such that, in step b), the modulation period is defined depending on the estimated heart rate.

According to one embodiment, step b) comprises an activation of the light source in an alarm sequence when:

an air flow rate measured in step a) is greater than a predefined flow-rate threshold value;

and/or a variation in the air flow rate, during a determined time range, is less than a variation threshold;

and/or an air pressure measured in step a) is less than a predefined pressure threshold value.

A third subject of the disclosure is a respiratory ventilation device, intended to send an airflow, generated by a fan, into a duct, the duct extending between the device and a respiratory mask, intended to be worn by a user, the device comprising an enclosure;

the enclosure extending, around a longitudinal axis, between a base and a top;

the enclosure comprising a side face connecting the base and the top, the side face extending around the longitudinal axis;

the enclosure comprising:

an air inlet, intended to admit air into the enclosure;

a fan;

an air outlet, the air outlet being configured to be connected to the duct;

such that when the fan is operating, air flows from the air inlet successively to the fan then to the air outlet;

the device being characterized in that:

the enclosure comprises at least one holder, forming a curve, and extending inside the enclosure, around the longitudinal axis, the holder being placed facing the side wall, the holder bearing a plurality of light sources, each light source being configured to emit a light;

the enclosure comprises a control unit, configured to activate the light sources;

the enclosure is formed from a translucent and/or scattering material;

such that under the effect of an activation of the light sources fastened to the holder, the light, produced by the light sources, diffuses through the side wall of the enclosure.

According to one embodiment, the side wall extends around the longitudinal axis at a first radius;

the enclosure contains a reflector of light, the reflector extending around the longitudinal axis, at a second radius less than the first radius;

such that the reflector is able to reflect a light produced by the light sources toward the enclosure.

The device may comprise any one of the following features, alone or in technically feasible combinations:

The light sources are configured to emit a light in the direction of the top of the enclosure.

At least one light source, or even each light source, emits a light in an emission cone extending around an emission axis, the emission axis of the light source, or of each light source, being oriented in the direction of the top of the enclosure.

The light sources are spaced apart around the longitudinal axis.

At least one light source, or even each light source, lies between the holder and the longitudinal axis, such that the holder is placed between at least one light source, or even each light source, and the enclosure. The holder may notably be opaque. It may then form an opaque strip.

The enclosure comprises a clock, connected to the control unit, such that the control unit is configured to modulate a light intensity of the light sources depending on the clock.

The control unit is configured to modulate a light intensity of the light sources with a modulation period, the modulation period comprising a gradual increase in light intensity followed by a gradual decrease in light intensity. The modulation period may be adjustable.

The control unit is configured to modulate a color of the light emitted by each light source.

According to one embodiment, the device comprises a flow sensor for measuring the flow rate of the air entering or exiting the device, the control unit being connected to the flow sensor, such that the control unit is configured to modulate a light intensity of the light sources depending on the flow rate measured by the flow sensor.

The control unit may be configured to:
determine a respiratory rate depending on the measurements of the flow sensor;
define the modulation period depending on the respiratory rate.

According to one embodiment, the device comprises a pressure sensor for measuring the pressure of the air blown by the device, the control unit being connected to the pressure sensor such that the control unit is configured to activate the light sources depending on the pressure measured by the pressure sensor.

Other advantages and features will become more clearly apparent from the following description of particular embodiments of the disclosure, which embodiments are given by way of nonlimiting examples, and shown in the figures listed below.

DETAILED DESCRIPTION

Figure 1A:
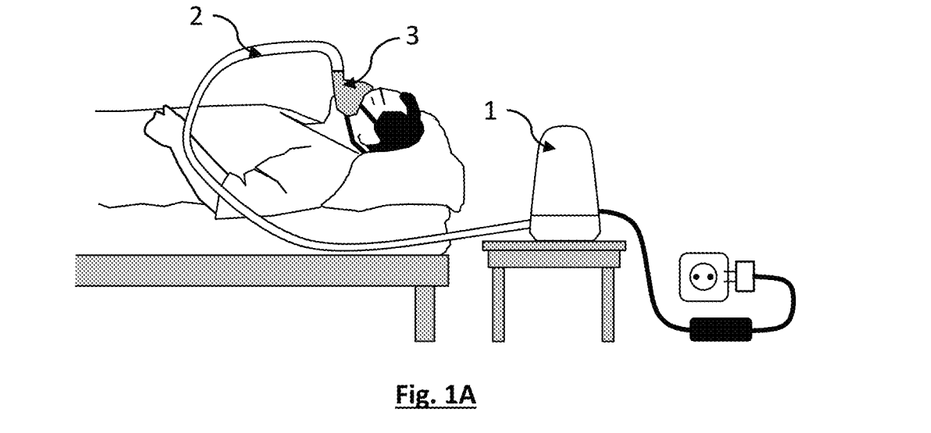
FIG. 1A is a schematic showing one use of the device.

FIG. 1A shows a device 1 for aiding breathing according to embodiments of the disclosure. The device comprises a duct 2, connecting it to a respiratory mask 3 intended to be applied to the face of a user. Preferably, the duct 2 is a flexible duct, the length of which is a few meters. The device 1 comprises a fan, controlled to maintain a setpoint pressure in the respiratory mask. It is essentially intended for use at night. During its use, the device may notably be placed on a planar holder, a bedside table for example.

Figure 1B:
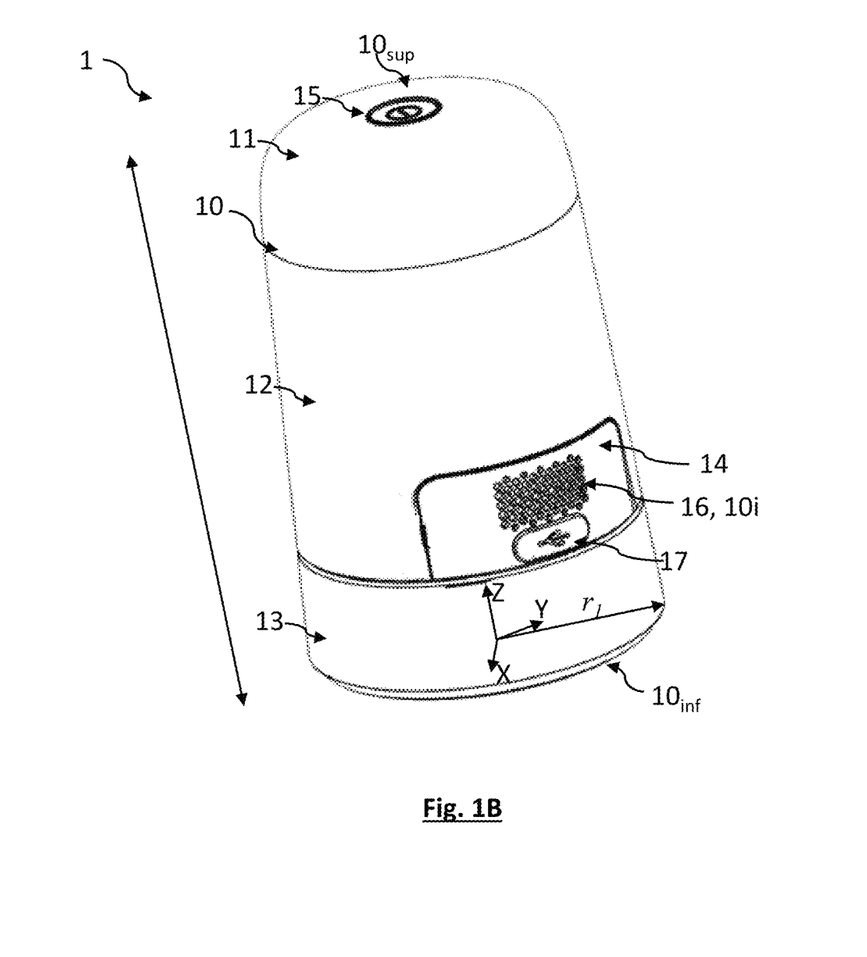
FIGS. 1B and 1C are views of the enclosure of the device.
Figure 1C:
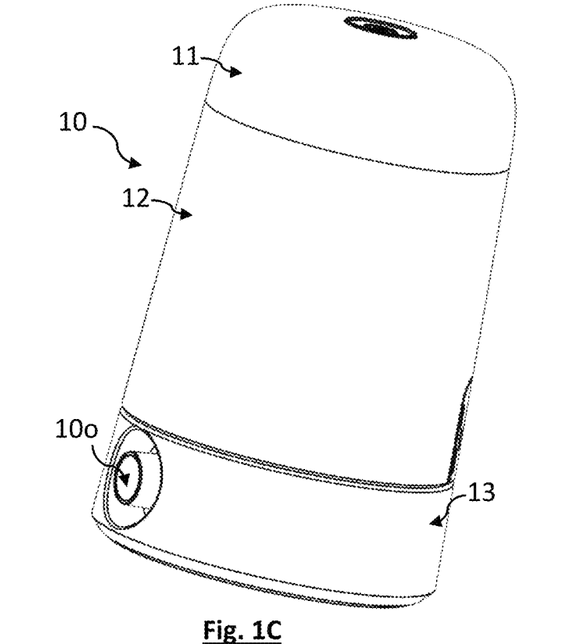

FIGS. 1B and 1C show an enclosure 10 of the device 1. The enclosure 10 extends along a longitudinal axis Z, thereby defining a length l, between a base $10_{inf}$ and a top $10_{sup}$. The enclosure extends radially in a base plane XY, in which it defines a first radius $r_1$. The length l is typically comprised between 10 cm and 40 cm, while the first radius $r_1$ is generally comprised between 5 cm and 30 cm. The dimensions of the device make it easily transportable. Moreover, the device is suitable for being placed on a planar holder of small dimensions, a table for example. In use, the longitudinal axis Z is preferably parallel to the vertical, while the base plane XY is horizontal.

The enclosure 10 is preferably made of a rigid material, a plastic for example. The material from which the enclosure is made is not opaque. Without however being transparent, it is a preferably a translucent and/or scattering material through which light diffuses: thus, it is not possible, from outside of the enclosure, to identify the components placed inside the latter. The enclosure may be transparent, but this does not correspond to the preferred embodiment. In the example shown, the enclosure 10 comprises a side wall, defining an upper section 11, an intermediate section 12 and a lower section 13. The lower section 13 is bounded by a lower surface, forming the base $10_{inf}$ of the enclosure. The base of the enclosure $10_{inf}$ is preferably planar and parallel to the base plane XY. The base of the enclosure $10_{inf}$ is intended to be placed on a planar holder.

The intermediate section 12 comprises a grille 16, which acts as a filter, and forms an air inlet 10i, through which air may penetrate into the enclosure 10. The intermediate section 12 also comprises a connection port 17, allowing a connection of the device 1 to a remote processing unit, with a view to configuration of a control unit 18 placed inside the enclosure 10 and described with reference to FIG. 1D.

In this example, the connection port 17 and the air inlet 10i are placed under a removable cover 14.

An on/off control switch 15 is placed on the upper section 11. The placement at the top of the enclosure 10 makes it easily accessible to a user, including in half-light or darkness. The control switch 15 may comprise a light source, a light-emitting diode for example, so as to be visible in the dark. The enclosure 10 is preferably symmetrical about the longitudinal axis Z. The on/off control switch is then centered on the longitudinal axis Z. Thus, whatever the rotation of the device 1, about the longitudinal axis Z, the on/off switch 15 does not move: its position is independent of the rotation of the device Z about the longitudinal axis Z.

In FIG. 1C, it may be seen that the lower section 13 comprise an outlet aperture forming an air outlet 10o of the device 1. The outlet aperture (air outlet 100) is intended to be connected to the duct 2, shown in FIG. 1A, during use of the device 1.

Figure 1D:
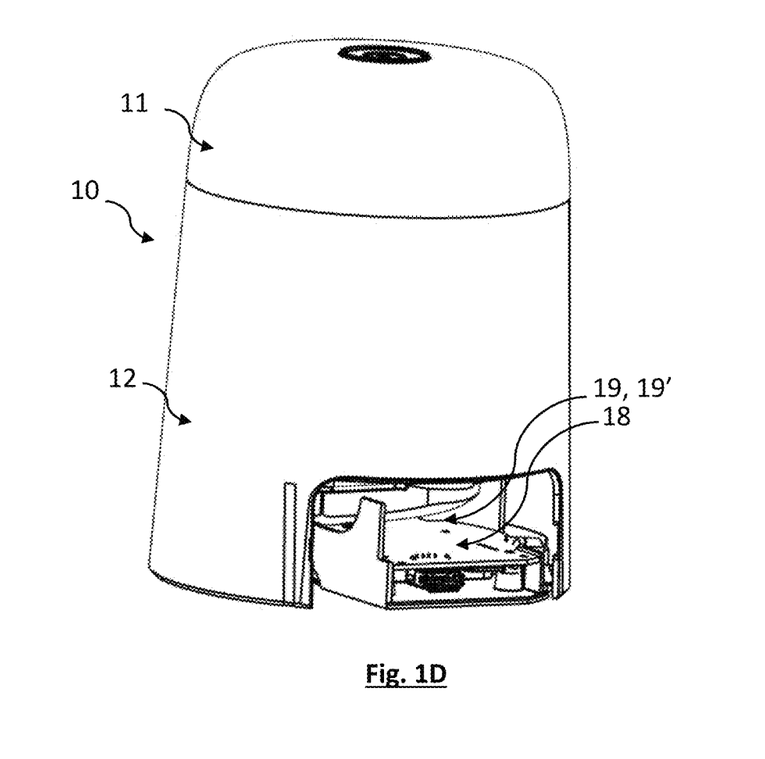
FIG. 1D shows one portion of the enclosure of the device, from which a removable cover has been removed.

FIG. 1D shows the intermediate section 12 and the upper section 11. In FIG. 1D, a control unit 18, which allows the device 1 to be configured and/or driven, and in particular the fan to be controlled, may be seen. The control unit 18 may be configured via a wired link connected to the connection port 17, as described above. The control unit 18 takes the form of a printed circuit board (PCB).

Figure 1E:
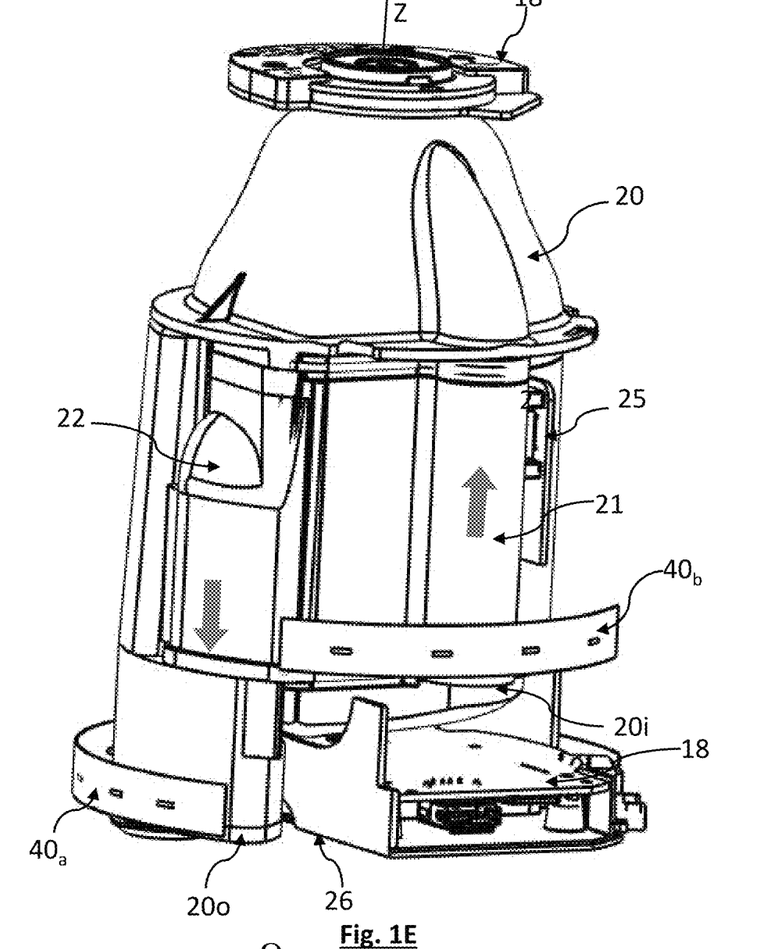
FIG. 1E shows components of the device that are located inside the enclosure.

FIG. 1E shows the inside of the intermediate section 12 and of the upper section 11. The air admitted into the enclosure 10, through the aperture (air inlet 10i), flows through an inlet tube 21, in the direction of the top of the device, parallel or substantially parallel to the longitudinal axis Z. The air is then admitted into a shell 20, in which lies a ventilation chamber, comprising the fan. In FIG. 1E, the fan is masked by the shell 20. The fan allows air to be drawn from the aperture (air inlet 10i) into the ventilation chamber. The fan generates an airflow that propagates through an outlet tube 22. The outlet tube opens into the lower section 13, via an aperture 20o. The aperture 20o is located at the interface between the intermediate section 12 and the lower section 13. The air, which enters into the lower section 13 through the aperture 20o, flows, in the lower section 13, toward the outlet aperture (air outlet 100).

The device also comprises an auxiliary circuit board 18, connected to the on/off switch 15. The auxiliary circuit board 18' is also connected to the control unit 18.

The device 1 comprises a flowmeter (flow sensor 25), connected to the control unit 18. The flowmeter (flow sensor 25) allows the flow rate of air propagating through the inlet tube 21, under the effect of the suction by the fan, to be measured. In this example, the flowmeter (flow sensor 25) is located next to the inlet tube 21. The flowmeter (flow sensor 25) allows a setpoint pressure of the air sent by the device 1 to the user's mask 3 to be adjusted. For example, when the user is a victim of a sleep apnea, the air flow rate drops, this leading to an increase in the setpoint pressure.

The device may comprise a pressure sensor 26, measuring the pressure of the air between the fan and the air outlet 10o. Depending on the measured pressure, a control unit changes the power of the fan so as to keep the pressure as stable as possible around the setpoint pressure.

The device is intended to be used in the dark. In order to be visible, the device comprises light sources 41 placed on at least one holder 40. In the example shown, the holder 40 describes a curve: the holder 40 is annular. By annular holder, what is meant is a holder describing all or part of a ring, around the longitudinal axis Z. In the example shown in FIG. 2A, the annular holder 40 comprises a first holder 40a, and a second holder 40b, the first holder and the second holder being separate, so as to conform to the geometry of the device.

FIG. 1E shows the placement of the first holder 40a, in the lower portion of the intermediate section 12, and the placement of the second holder 40b, above the control unit 18. The light sources 41 are connected to an activating circuit 19, which forms part of the control unit 18, allowing their activation and a potential modulation of their intensity.

Figure 2A:
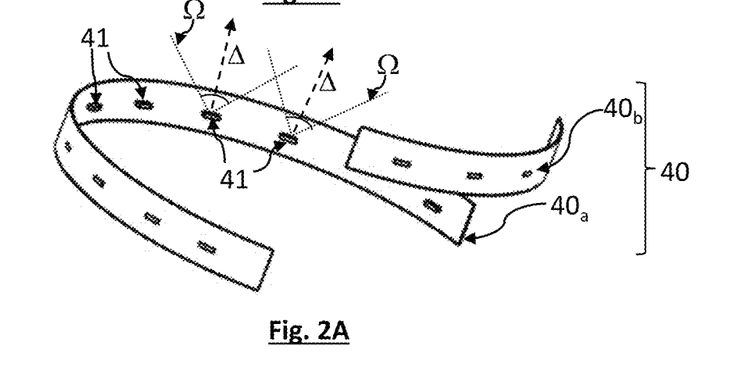
FIG. 2A shows a holder to which light sources are fastened.

Each annular holder comprises at least one light source 41. Each light source 41 is, for example, a light-emitting diode. Preferably, the light sources are spaced regularly apart on an annular holder. Preferably, the holder 40 is arranged such that the light sources 41 are distributed, preferably regularly, around the longitudinal axis Z. In the example shown, the first holder 40a comprises 11 regularly spaced light sources 41. The second holder 40b comprises 4 regularly spaced light sources 41. Placing a plurality of light sources on the same holder makes manufacture simpler and less expensive. In the remainder of the description, the holder 40 designates the assembly formed by the first holder 40a and the second holder 40b. The holder 40 may be flexible, this making it less expensive to manufacture.

The holder 40 defines a curve. Each light source is oriented inside of a convex space bounded by the curve. Thus, each light source is placed inside a convex space bounded by the holder 40, between the latter and the longitudinal axis Z. Thus, the holder 40 is interposed between the enclosure 10 and the light sources. The holder 40 is advantageously opaque. It then forms an opaque strip interposed between the luminous portion of each light source 41 and the enclosure 10. Thus, the light emitted by each light source reaches the enclosure 10 indirectly, via reflection or backscatter, as explained below. The height of the holder, parallel to the longitudinal axis Z, is preferably comprised between 1 and 5 cm, preferably between 1 and 3 cm.

Preferably, each light source 41 generates light in an emission cone a extending around an emission axis A. The emission axis Δ associated with each light source 41 is parallel, or substantially parallel, to the longitudinal axis Z, toward the upper section 11 of the enclosure 10. Thus, the light emitted by each light source 41 propagates, during emission, toward the upper section 11 (or toward the top $10_{sup}$ of the enclosure 10). In the example shown, the light sources are so-called "side-emitting" light-emitting diodes. Due to the opening angle of the emission cone Ω, the light emitted by each light source 41 is backscattered either by the holder 40 (in the present case the first holder 40a or the second holder 40b), or by a reflector 30 described with reference to FIGS. 2B and 2C. In FIG. 2A, two emission cones Q have been shown, these cones being respectively associated with two light sources 41, and centered on emission axes Δ oriented toward the upper section 11 of the enclosure 10.

Figure 2B:
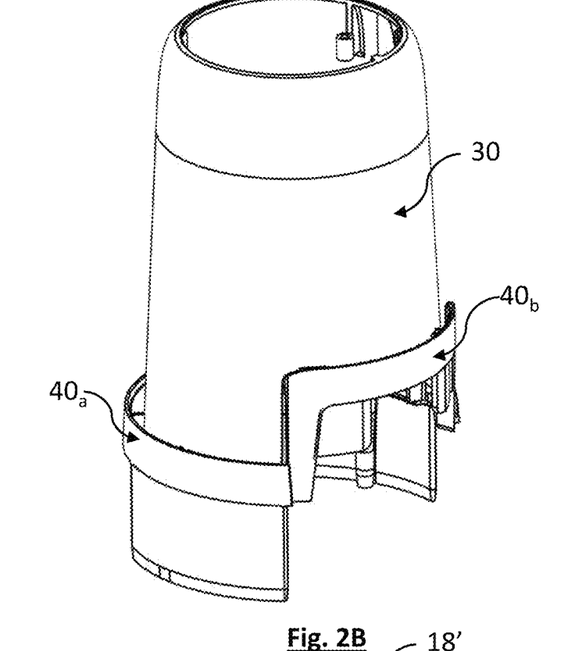
FIGS. 2B and 2C show a reflector around which the holder is placed.
Figure 2C:
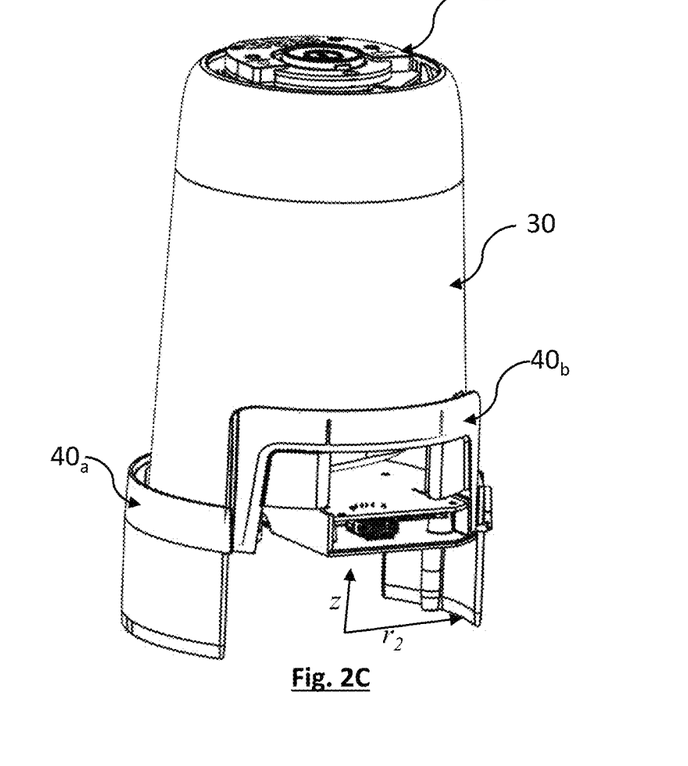

FIGS. 2B and 2C represent the, scattering or opaque, reflector 30 covering the shell 20 shown in FIG. 1E, and the inlet and outlet tubes 21, 22. The reflector 30 is encircled by the holder 40. In the example shown, the reflector 30 has a tubular geometry, with a second radius $r_2$ strictly less than the first radius $r_1$ of the enclosure 10. The reflector 30 is dimensioned to allow the holder 40 to be interposed between the enclosure 10 and the reflector 30. The reflector 30 lies facing the light sources 41 borne by the holder 40. The function of the reflector 30 is to reflect, or to backscatter, the light emitted by each light source 41 toward the enclosure 10. Due to the arrangement of the holder 40, of the light sources 41 and of the reflector 30, the holder 40 forms an opaque mask preventing the light emitted by each light source 41 from reaching the enclosure 10 directly, before being reflected or backscattered by the reflector 30. Thus, most of the light, emitted by the light sources 41 and that reaches the enclosure 10, is reflected or backscattered by the reflector 30. The light (from light source 41) thus reaches the enclosure 10 indirectly. Some of the light reaching the enclosure 10 diffuses through the latter to outside of the enclosure. The rest of the light reaching the enclosure 10 is backscattered by the latter toward the reflector 30. Thus, seen from the outside, the enclosure 10 forms a secondary light source, generating diffuse lighting. A device of pleasant appearance and with no hot spots, i.e., with no local non-uniformities in illumination, likely to discomfort the user is obtained as a result. Inside the enclosure 10, the light propagates between the reflector 30 and the enclosure 10, in the direction of the top $10_{sup}$ of the enclosure 10.

The height of the reflector 30, parallel to the longitudinal axis Z, is comprised between the height of the holder 40 and that of the enclosure 10. Preferably, it corresponds to at least 50% of the height of the enclosure 10. Preferably, the height of the reflector 30 is at least three or four times greater than the height of the holder 40.

Due to the arrangement described above, the light sources 41, the holder 40 and the reflector 30 are not perceptible from outside of the enclosure 10. The secondary lighting produced by the enclosure 10, which lighting is formed by the light diffusing through the intermediate section 12 of the enclosure 10, forms a gradient, the diffused intensity increasing with distance from the upper section 11. By secondary light source or secondary lighting, what is meant is that the light is not emitted by the enclosure 10, but simply diffused by the latter, toward the outside of the enclosure 10, and in particular toward the user.

Due to the presence of opaque elements placed between the holder 40 and the lower section 13 of the enclosure 10, little or no light reaches the lower section 13 of the enclosure 10.

In FIG. 2C, the auxiliary board 18' has been shown, placed inside the enclosure 10, in the upper section 11.

Figure 2D:
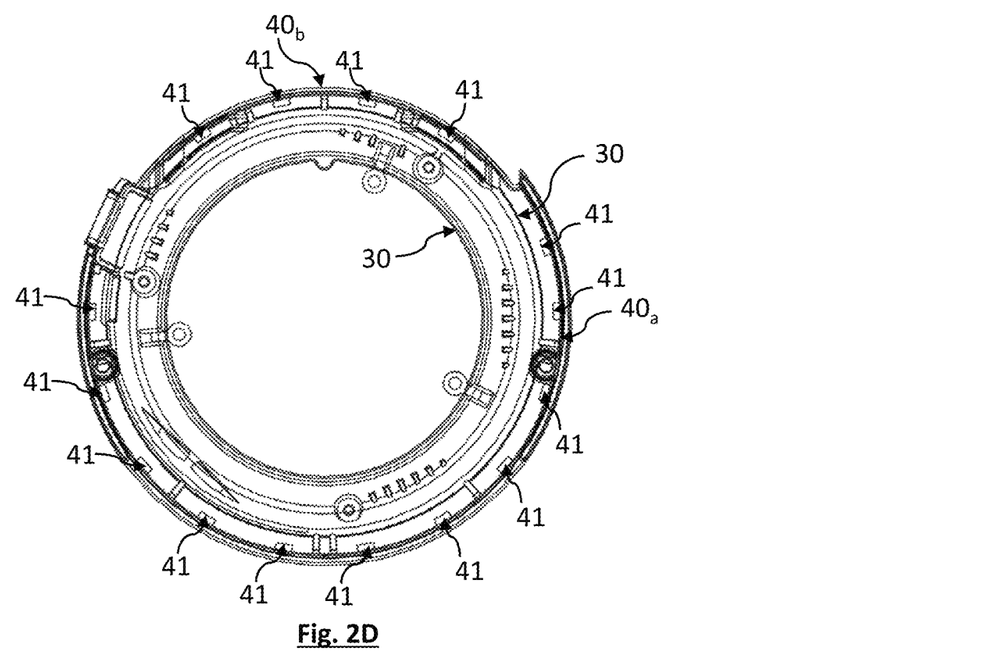
FIG. 2D is a view from above, showing the arrangement of the light sources, borne by the holder, around the reflector.

FIG. 2D is a view from above of the reflector 30 and of the holder 40 (first holder 40a and second holder 40b) bearing the light sources 41. The distribution of the light sources 41 around the reflector 30, in a space comprised between the holder 40 and the reflector 30, may be seen.

Figure 3:
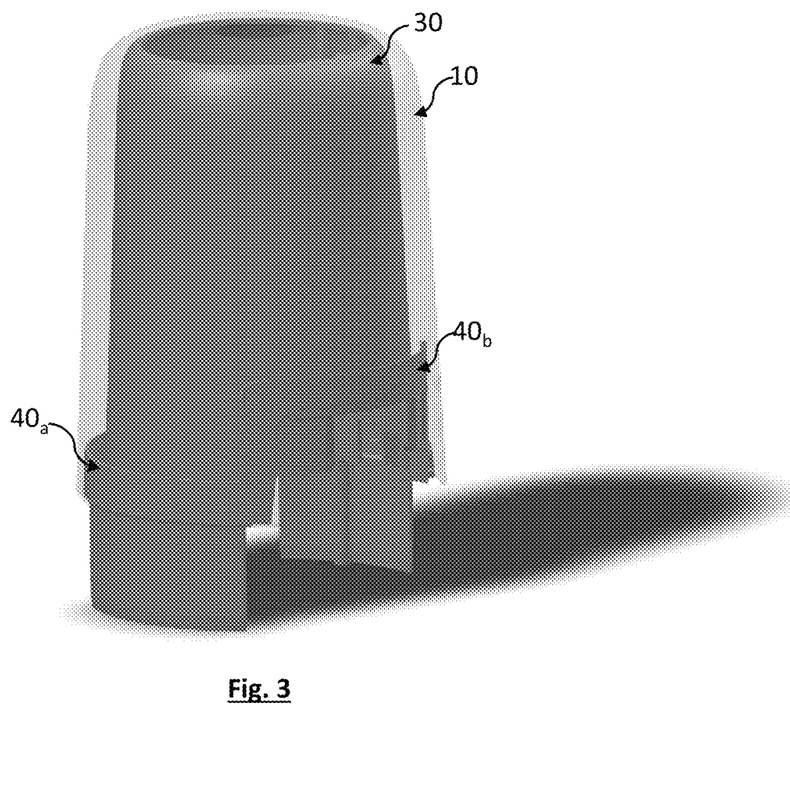
FIG. 3 shows, drawn so that it may be seen through, the enclosure, inside of which lie the reflector and the holder of the light sources.

FIG. 3 shows, drawn so that it may be seen through, the enclosure 10, which is superimposed on the reflector 30. As described above, the enclosure 10 forms a diffuser for the light reflected or backscattered by the reflector 30. It allows light to be diffused to the outside of the enclosure 10, thus forming a secondary light source.

Figure 4:
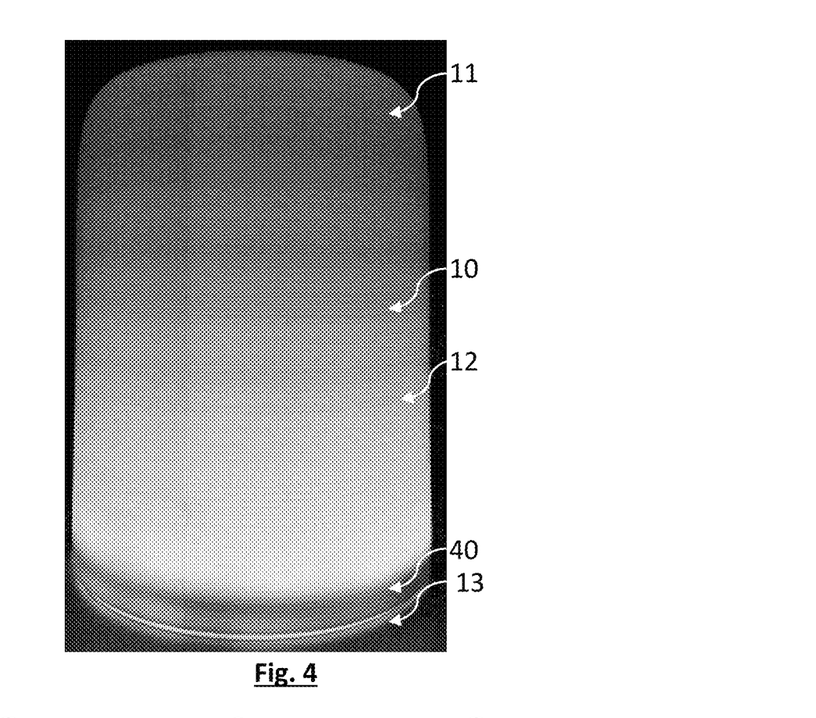
FIG. 4 is a view of the outside of the enclosure.

FIG. 4 is a photograph of an example of an enclosure 10 according to embodiments of the disclosure. The upper section 11, intermediate section 12 and lower section 13 of the enclosure 10, and the holder 40, may be seen. It may be seen that the device allows a light-intensity gradient to be obtained.

The light emitted by the device 1 may have a plurality of functions, which are described below.

It may act as a lamp providing lighting, as a bedside lamp would. It may also be connected to a clock 19', located in the enclosure, and, for example, near the control unit 18. In the example shown, the clock is placed on the control unit 18. Depending on the time indicated by the clock 19', the control unit may gradually activate the light sources 41, while modulating the emitted light intensity. An operating mode similar to that of a dawn simulator is then obtained.

Figure 5A:
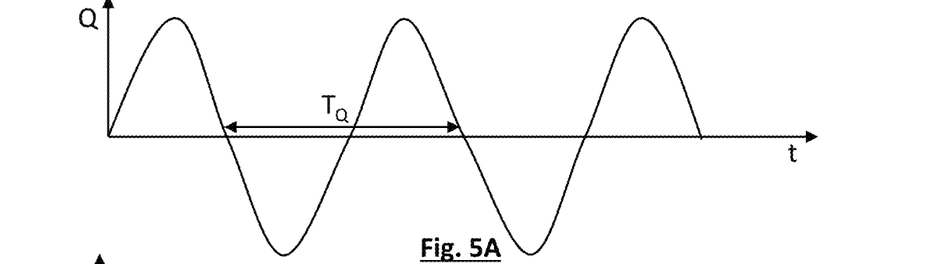
FIG. 5A schematically shows a measurement of an air flow rate resulting from a flowmeter placed in the device.
Figure 5B:
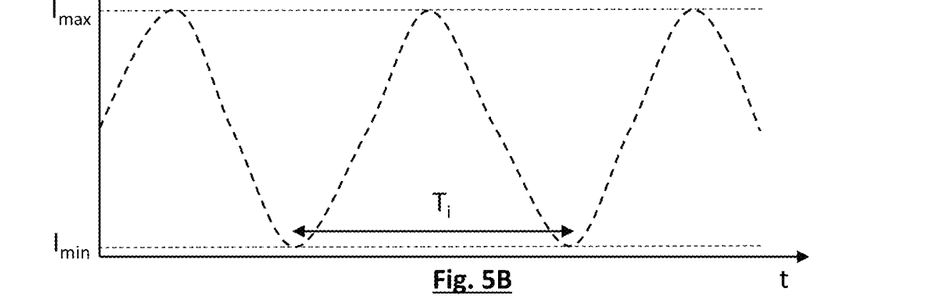
FIG. 5B schematically shows a modulation of the light intensity of the light sources.

According to one embodiment, schematically shown in FIGS. 5A and 5B, the device allows the light intensity of the light sources 41 to be modulated, with a regular illumination period $T_i$, such that the user may match his exhalation and inhalation to the modulation frequency. FIG. 5A shows a variation as a function of time in the air flow rate Q measured by the flow sensor. FIG. 5B illustrates a variation in the intensity of the light sources. Thus, the device forms a metronome defining a respiratory rate $T_Q$ that is predetermined, and optionally adjustable, manually for example. For example, each modulation period $T_i$ comprises a phase in which light intensity gradually increases, passing from a minimum intensity $I_{min}$ to a maximum intensity $I_{max}$, followed by a phase in which light intensity gradually decreases, passing from the maximum intensity Imax to the minimum intensity $I_{min}$. The modulation period $T_i$ may typically be comprised between 3 s and 15 s. It is generally accepted that a user's respiratory rate is around 10 s, or 6 breaths per minute. For example, in one half-period, the user inhales (or exhales) under the effect of the increase in light intensity. In the other half-period, the user exhales (or inhales), under the effect of the decrease in light intensity.

Alternatively or in addition, during the modulation period, the color of one or each light source gradually varies between a start color (blue, for example) and an end color (red, for example), then from the end color to the start color.

During the same illumination period $T_i$, the phases in which the light intensity increases and decreases may be of same duration, or be of different durations, the increase, for example, taking longer than the decrease or vice versa. Depending on the modulation of the light intensity, the user may adapt his breathing, this allows a relaxing effect to be achieved, according to the principles of cardiac coherence. This may help the user to fall asleep. The modulation of the intensity and/or the color of the light sources may be adjustable by the patient.

According to one embodiment, the modulation of each light source is controlled by the flow sensor 25. Specifically, the measurement given by the flow sensor 25 allows a respiratory rate $T_Q$ of the user to be estimated. The modulation period $T_i$ may be defined depending on the respiratory rate $T_Q$ of the user, in particular to gradually slow down the respiratory rate. Thus, depending on the measurements delivered by the flow sensor 25, the control unit 18 defines a modulation period $T_i$ of the light intensity that is slower than the respiratory rate $T_Q$, until the respiratory rate $T_Q$ measured by the flow sensor is within a predetermined acceptable range.

According to another embodiment, from the flow rate measured by the flowmeter, it is possible to estimate a heart rate HR of the user. The modulation period is then adjusted, by the control unit 18, so as to adapt the modulation period $T_i$ of the light sources depending on the heart rate. The modulation period preferably corresponds to a respiratory rate suitable for the heart rate.

Figure 6A:
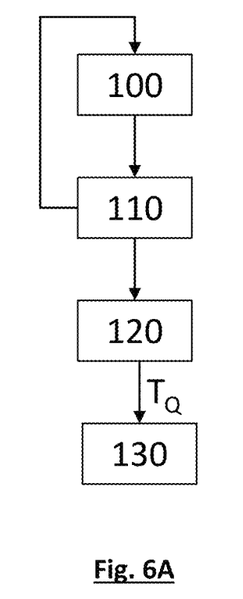
FIGS. 6A and 6B schematically show sequences of steps implementing flow-rate or pressure measurements.

FIG. 6A summarizes the main steps of the embodiments described above:
Step 100: measurement of the air flow rate by the flow sensor at a measurement time;
Step 110: reiteration of step 100;
Step 120: on the basis of a plurality of measurements of air flow rate at various measurement times, estimation of a respiratory rate $T_Q$, and possibly of a heart rate HR;
Step 130: adaptation of the modulation period $T_i$ depending on the estimations of the respiratory rate $T_Q$ or of the heart rate HR.

According to one embodiment, the flow sensor 25 is connected to the control unit 18. In case of inadvertent removal of the mask, the pressure measured by the pressure sensor 26 tends to decrease, this leading to an increase in the speed of the fan so that the measured pressure corresponds to the setpoint pressure. Thus, the air flow rate, measured by the flow sensor 25, increases. Beyond a flow-rate threshold value, the device goes into alarm. The control unit activates the light sources in an alarm sequence, for example by modifying the color (or intensity) of the emitted light, the light possibly, for example, being red. The flow-rate threshold value may be defined beforehand. When the air flow rate, measured by the flow sensor 25, is normal, the light emitted by the light sources may be blue or white. The term alarm sequence designates an activation of the light source representative of an alarm, for example a red and/or rapidly flashing light, etc.

According to one embodiment, the pressure sensor 26 is connected to the control unit 18. In case of inadvertent removal of the mask, the pressure measured by the pressure sensor 26 may no longer be the setpoint pressure, and drop below the setpoint pressure. In case of a drop in measured pressure below a pressure threshold value, likely to correspond to an inadvertent removal of the mask 3, the control unit 18 activates the light sources 41, in the alarm sequence. The threshold pressure may be defined beforehand.

More generally, it is possible to define an acceptable flow-rate range, and to activate the light sources in the alarm sequence when the flow rate measured by the flow sensor 25 exits from the flow-rate range. Analogously, it is possible to define an acceptable pressure range, and to activate the light sources in the alarm sequence when the pressure measured by the pressure sensor 26 exits from the pressure range.

According to another embodiment, a removal of the mask may be detected by the flow sensor, in particular by analyzing variations as a function of time in the flow rate measured during a time range. When the flow rate is stable, this may be the result of an inadvertent removal of the mask. Thus, when the variations as a function of time in the flow rate are not sufficiently marked in a predetermined period of time, i.e., when the variations as a function of time are less than a predetermined variation threshold, the light sources may be activated in the alarm sequence.

Figure 6B:
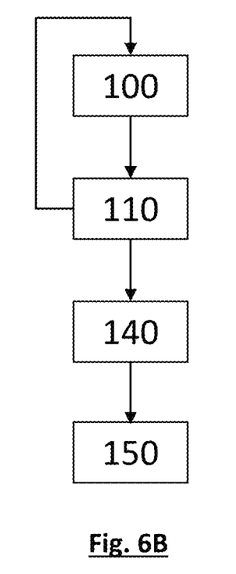

FIG. 6B summarizes the main steps of the embodiment described above:

Step 100: measurement of the air flow rate by the flow sensor and/or of the air pressure by the pressure sensor, at a measurement time;

Step 110: reiteration of step 100;

Step 140: comparison of each measured flow rate or of each measured pressure with a threshold value or with a range of values. This step may comprise a determination of a variation in various measured flow rates and a comparison of the variation with a variation threshold.

Step 150: depending on the comparison, activation of an alarm sequence.

In the examples described above and illustrated in FIGS. 1 to 4, the enclosure 10 has a substantially cylindrical shape. Other shapes are naturally envisionable, for example a hemispherical shape or a conical shape.

The invention claimed is:

1. A respiratory ventilation device, configured to send an airflow, generated by a fan, into a duct, the duct extending between the device and a respiratory mask, configured to be worn by a user, the device comprising:
   an air inlet, intended to admit air into the device;
   a fan;
   an air outlet, the air outlet being configured to be connected to the duct;
      such that when the fan is operating, air flows, through the device, from the air inlet successively to the fan then to the air outlet;
   a flow sensor, configured to measure a flow rate of air flowing through the device, and/or a pressure sensor, configured to measure a pressure between the fan and the air outlet;
   a control unit, connected to the flow sensor and/or to the pressure sensor;
the device further comprising an enclosure, defining the air inlet and the air outlet, the enclosure containing the fan,
   the enclosure extending, around a longitudinal axis, between a base and a top;
   the enclosure comprising a side wall connecting the base and the top, the side wall extending around the longitudinal axis;
   the enclosure comprising at least one holder, forming a curve, and extending inside the enclosure, around the longitudinal axis, the holder being placed facing the side wall, the holder bearing a plurality of light sources, each light source being configured to emit a light;
   the enclosure being formed from a translucent and/or scattering material;
   such that under the effect of an activation of the light sources fastened to the holder, the light, produced by the light sources, diffuses through the side wall of the enclosure; and
wherein:
   the side wall extends around the longitudinal axis at a first radius;
   the enclosure contains a light reflector, the light reflector extending around the longitudinal axis, at a second radius less than the first radius;
   such that the light reflector is configured to reflect a light produced by the light sources toward the enclosure.

2. The device of claim 1, wherein the light sources are configured to emit the light in the direction of the top of the enclosure.

3. The device of claim 1, wherein at least one light source, or each light source, emits light in an emission cone extending around an emission axis, the emission axis of the light source, or of each light source, being oriented in the direction of the top of the enclosure.

4. The device of claim 1, wherein the light sources are spaced apart around the longitudinal axis.

5. A respiratory ventilation device, configured to send an airflow, generated by a fan, into a duct, the duct extending between the device and a respiratory mask, configured to be worn by a user, the device comprising:
   an air inlet, intended to admit air into the device;
   a fan;
   an air outlet, the air outlet being configured to be connected to the duct;
   such that when the fan is operating, air flows, through the device, from the air inlet successively to the fan then to the air outlet;
      a flow sensor, configured to measure a flow rate of air flowing through the device, and/or a pressure sensor, configured to measure a pressure between the fan and the air outlet;
      a control unit, connected to the flow sensor and/or to the pressure sensor;
   the device further comprising an enclosure, defining the air inlet and the air outlet, the enclosure containing the fan,
      the enclosure extending, around a longitudinal axis, between a base and a top;
      the enclosure comprising a side wall connecting the base and the top, the side wall extending around the longitudinal axis;
      the enclosure comprising at least one holder, forming a curve, and extending inside the enclosure, around the longitudinal axis, the holder being placed facing the side wall, the holder bearing a plurality of light sources, each light source being configured to emit a light;
      the enclosure being formed from a translucent and/or scattering material;
   such that under the effect of an activation of the light sources fastened to the holder, the light, produced by the light sources, diffuses through the side wall of the enclosure;
wherein at least one light source, or each light source, lies between the holder and the longitudinal axis, such that the holder is interposed between at least one light source, or each light source, and the enclosure.

6. The device of claim 1, wherein at least one light source is driven by the control unit, such that the control unit is configured to activate the light source depending on the flow rate of air measured by the flow sensor and/or on the pressure measured by the pressure sensor.

7. The device of claim 1, wherein the control unit is configured to modulate a color of the light emitted by the light source.

8. The device of claim 1, wherein the control unit is configured to modulate a light intensity and/or a color of the light source with a modulation period, the modulation period comprising:
   a gradual increase in light intensity followed by a gradual decrease in light intensity;

and/or a gradual variation in color between a start color and an end color, followed by a gradual variation in the color of the emitted light between the end color and the start color.

9. The device of claim 8, wherein the modulation period is adjustable.

10. The device of claim 6, wherein the control unit is configured to:
estimate a respiratory rate depending on the measured flow rates of the flow sensor;
define the modulation period depending on the estimated respiratory rate.

11. The device of claim 6, wherein the control unit is configured to:
estimate a heart rate depending on the flow rates measured by the flow sensor;
define the modulation period depending on the estimated heart rate.

12. The device of claim 6, wherein the control unit is configured to activate the light source, in an alarm sequence, when the air flow rate is outside of a predetermined flow-rate range.

13. The device of claim 6, wherein the control unit is configured to determine a variation as a function of time in the flow rates measured by the flow sensor, at various successive times, and to activate the light source, in an alarm sequence, when the variation as a function of time is less than a predefined variation threshold.

14. The device of claim 6, wherein the control unit is configured to activate the light source, in an alarm sequence, when the air pressure is outside of a predetermined pressure range.

15. The device of claim 1, wherein the enclosure comprises a clock, connected to the control unit, such that the control unit is configured to modulate a light intensity of the light sources depending on the clock.

16. A method for controlling a light source of the device of claim 1, comprising:
a) measuring flow rates using the flow sensor and/or of pressures using the pressure sensor at various measurement times, respectively;
b) depending on the measured flow rates and/or pressures, activating the light source with the control unit.

17. The method of claim 16, wherein, in b), activating the light source is configured to modulate a light intensity and/or a color of the light source with a modulation period, the modulation period comprising:
a gradual increase in light intensity followed by a gradual decrease in light intensity;
and/or a gradual variation in color between a start color and an end color, followed by a gradual variation in the color of the emitted light between the end color and the start color.

18. The method of claim 17, wherein a) comprises
measuring flow rates at various measurement times, and an estimating a respiratory rate depending on the measured flow rates, such that, in b), the modulation period is defined depending on the estimated respiratory rate; and/or
measuring flow rates at various measurement times, and estimating a heart rate depending on the measured flow rates, such that, in b), the modulation period is defined depending on the estimated heart rate.

19. The method of claim 16, wherein b) comprises activating the light source in an alarm sequence when:
an air flow rate measured in step a) is outside of a predetermined flow-rate range;
and/or a variation in the air flow rate, during a determined time range, is less than a variation threshold;
and/or an air pressure measured in a) is outside of a predetermined pressure range.

* * * * *